(12) United States Patent
Abuto et al.

(10) Patent No.: US 6,503,854 B1
(45) Date of Patent: Jan. 7, 2003

(54) ABSORBENT COMPOSITE MATERIALS

(75) Inventors: Frank Paul Abuto, Duluth, GA (US); Marcille Faye Ruman, Oshkosh, WI (US); Anthony John Wisneski, Kimberly, WI (US); Yong Li, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 181 days.

(21) Appl. No.: 09/611,005

(22) Filed: Jul. 6, 2000

Related U.S. Application Data (63) Continuation-in-part of application No. 08/962,024, filed on Oct. 31, 1997, now abandoned.

(51) Int. Cl.[7] .............................. A61F 5/44; A61F 13/15
(52) U.S. Cl. .................... 442/149; 442/414; 604/365; 604/368; 604/372; 604/387
(58) Field of Search ................. 442/118, 149, 442/389, 414; 604/365, 358, 372, 387

(56) References Cited

U.S. PATENT DOCUMENTS

| | | | |
|---|---|---|---|
| 2,357,392 A | * | 9/1944 | Francis, Jr. |
| 4,100,324 A | * | 7/1978 | Anderson et al. |
| 4,383,376 A | * | 5/1983 | Numamoto et al. |
| 4,392,908 A | * | 7/1983 | Dehnel |
| 4,540,454 A | | 9/1985 | Pieniak et al. |
| 4,560,372 A | * | 12/1985 | Pieniak |
| 4,600,462 A | * | 7/1986 | Watt |
| 4,675,209 A | * | 6/1987 | Pedigrew |
| 5,363,604 A | * | 11/1994 | Heyer |
| 5,409,768 A | * | 4/1995 | Dickenson et al. |
| 5,531,728 A | * | 7/1996 | Lash |
| 5,556,392 A | | 9/1996 | Koczak |
| 5,641,441 A | * | 6/1997 | Yang |

FOREIGN PATENT DOCUMENTS

| | | | |
|---|---|---|---|
| EP | 202 472 | | 11/1986 |
| EP | 518 291 | | 12/1992 |
| EP | 633 009 | | 1/1995 |
| GB | 2272916 | | 6/1994 |
| GB | 2280115 | * | 1/1995 |
| GB | 2284551 | | 6/1995 |
| WO | 89/10109 | * | 11/1989 |
| WO | 90 05808 | | 5/1990 |
| WO | 90/11170 | * | 10/1990 |
| WO | 90/11171 | * | 10/1990 |
| WO | 90/11181 | * | 10/1990 |
| WO | 90/11184 | | 10/1990 |
| WO | 91 10413 | | 7/1991 |

* cited by examiner

*Primary Examiner*—Daniel Zirker
(74) *Attorney, Agent, or Firm*—Pauley Petersen Kinne & Erickson (57) ABSTRACT

An absorbent composite material composed of a fibrous absorbent material and a binding agent, the binding agent binding at least a portion of the fibers of the fibrous absorbent material. The fibrous absorbent material is preferably selected from the group consisting of fluff pulp, synthetic fibers, natural fibers, and combinations thereof. The material suitable for use as an absorbent in personal care absorbent articles such as diapers, training pants, and adult incontinence garments.

47 Claims, 4 Drawing Sheets

ABSORBENT COMPOSITE MATERIALS

CROSS-REFERENCE TO RELATED U.S. PATENT APPLICATION

This application is a continuation-in-part application of U.S. patent application Ser. No. 08/962,024 filed Oct. 31, 1997 now abandoned.

BACKGROUND OF THE INVENTION

CROSS-REFERENCE TO RELATED U.S. PATENT APPLICATION

This application is a continuation-in-part application of co-pending U.S. patent application Ser. No. 08/962,024 filed Oct. 31, 1997.

1. Field of the Invention

This invention relates to an absorbent composite material which is particularly suitable for use in diapers, training pants, adult incontinence products, and the like. The absorbent composite material of this invention provides absorbent cores for such personal care absorbent articles having improved integrity, resistance to wet collapse, shape retention, and uptake rate. In addition, the material serves as a controlled rate retention material, exhibiting a controlled release swelling mechanism which is particularly suitable for diapers and other such personal care absorbent articles.

2. Description of Prior Art

Disposable absorbent articles such as diapers, training pants, adult incontinence garments, and the like have been known for some time. These products include an absorbent material which is used to absorb and hold or contain body fluids. Initially, in many of these products, the absorbent material comprised what is termed "wadding" or plies of tissue. The wadding was disposed between a liquid-impermeable backing and a liquid-permeable facing and the plies of tissue were used to absorb and contain the liquid within the product.

Products using wadding-type absorbent materials were replaced, for the most part, by an improved absorbent material comprising "fluffed wood pulp fibers". This absorbent material comprises a layer of individualized wood pulp fibers, with the layer having substantial thickness. This material provided personal care articles with the improved absorbent capacity and somewhat better containment than personal care articles using the wadding-type material. In addition, the fluffed wood pulp layer is quite soft, flexible, and conformable and, thus, produces an improved personal care article over personal care articles using wadding as the absorbent layer.

Although fluffed wood pulp absorbent materials provide improved capacity, the efficiency with which the capacity is used in personal care articles such as diapers is poor. This is due, in part, to the fact that the fluffed wood pulp absorbent material tends to break apart upon flexing and that once the absorbent material has accepted a substantial amount of liquid, the cellulosic fibers tend to collapse, sometimes causing liquid to be squeezed from the product and to leak. In addition, the fluid to be absorbed is generally deposited in a localized area and the ability of the fluid to move along the plane of the material is poor. U.S. Pat. No. 4,560,372 discloses an absorbent material of a layered structure for addressing these issues, the layered structure comprising a first fibrous layer substantially of resilient fibers and containing at least about 10% by weight of a superabsorbent material and a second layer of hydrophilic porous material substantially co-extensive with the first layer and superposed on the first layer.

Superabsorbents are polymers that are able to absorb fluid in quantities corresponding to many times their weight. They are also able to retain the absorbed fluid, even when subjected to external pressure. Such polymers have found wide use in absorbent personal care products such as diapers, sanitary pads and the like. These polymers are normally in particle form, such as in the form of grains, granules, flakes or fibers, and are typically layered or mixed with other absorbent materials, for example cellulose fibers.

The effectiveness of such superabsorbents in an absorbent material is contingent upon many factors including where and how the superabsorbent is incorporated into the absorbent material, its particle form and physical and chemical properties, and also the speed at which it absorbs fluids, its gel strength and its ability to retain absorbed fluids. One problem negatively affecting the absorbency of the absorbent material containing superabsorbents is that the superabsorbent particles located in a wetting region of the absorbent material bind the fluid in this region upon the first insult, thereby reducing the effectiveness of the material to absorb subsequent insults. As a result, the total absorption capacity of the absorbent body is not utilized to an optimal extent, thereby increasing the risk of fluid leakage from the article. This problem is even more acute where the articles are intended to be worn for extended periods of time, such as through the night during which wetting often occurs on several occasions.

Fluid distribution and material utilization are two critical performance measures for absorbent products such as diapers. It has been observed that the majority of soiled diapers exhibit uneven fluid distribution. Typically, the back portion of the diaper contains little or no absorbed fluid compared to the front/target area. As a result, there is severe under utilization of the absorbent material due to this inefficient fluid handling.

The movement of fluid away from the target zones requires the presence of two key functionalities—1) fluid handling or "distribution" throughout the entire product length and width and 2) "slow absorption" retention material located in the target zone. The advantages of using delayed absorption superabsorbent materials in diapers is taught, for example, by British Patent Application GB-2-280-115-A. A slow absorbing retention material has the potential for higher absorbency rates while reducing product performance deterioration typically associated with later insults.

The Absorbency Time Index of a material is defined as:

$$\text{Absorption Time Index} = (t_{20} + t_{40} + t_{60} + t_{80})/4$$

where $t_i$ is the time it takes for the material saturation to reach i% of the final (200 minute) value. Known superabsorbents such as STOCKHAUSEN FAVOR 836® and STOCKHAUSEN FAVOR 870®, available from Stockhausen in Greensboro, N.C., and DOW DRY TECH 2035®, available from Dow have very fast Absorption Time Indexes in the range of about 2.7 to about 4.0 minutes. STOCKHAUSEN FAVOR 836, STOCKHAUSEN FAVOR 870, and DOW DRYTECH 2035 are all water swellable, water insoluble, weakly crosslinked sodium polyacrylate polymers.

Samples based upon the teachings of U.S. Pat. No. 4,560,372 to Pieniak, UK Patent Application GB-2-280-115-A, and International Publication Number WO 91/10413 were prepared and evaluated with respect to Absorption Time Index of the disclosed materials. As shown in Table 1 hereinbelow, which summarizes the results obtained, the Absorption Time Index (ATI) for each of the disclosed materials was less than 2.6.

TABLE 1

Composite ATI Values (minutes)

| Sample | t20 | t40 | t60 | t80 | ATI= (t20 + t40 + t60 + t80)/4 |
|---|---|---|---|---|---|
| WO91/10413 - Codes 1 and 3 Combined | 0.12 | 0.34 | 0.92 | 3.67 | 1.26 |
| WO91/10413 - Codes 2 and 4 Combined | 0.48 | 0.57 | 1.28 | 2.33 | 1.16 |
| WO91/10413 - Codes 1 and 3 Combined | 0.37 | 0.60 | 0.90 | 3.83 | 1.42 |
| WO91/10413 - Codes 2 and 4 Combined | 0.25 | 0.39 | 0.78 | 3.67 | 1.27 |
| GB 2284551 - Code 2 | 0.30 | 0.87 | 2.83 | 6.25 | 2.56 |
| GB 2284551 - Code 3 | 0.06 | 0.22 | 1.01 | 4.33 | 1.41 |
| Pieniak 4,560,372 - Code 1 | 0.28 | 0.85 | 1.98 | 5.25 | 2.09 |

Samples Based Upon WO 91/10413

The materials used in the preparation of samples Code 1–4 were as follows:

Binder—35% solids ADCOTE 50T4990 available from Rohm and Haas Co.
SAP—FAVOR 880 available from Stockhausen
Fluff—NB416 available from Weyerhaeuser
Surfactant—Sodium dioctyl Sulfosuccinate 75.0% total solids from American Cynamid The proportions thereof for each sample are shown in Table 2.

TABLE 2

| Code | % Binder | % SAP | % Fluff | GSM | Density $g/in^2$ | Description |
|---|---|---|---|---|---|---|
| 1 | 20 | 50 | 30 | 500 | 0.2 | Insert pad |
| 2 | 10 | 50 | 40 | 500 | 0.2 | Insert pad |
| 3 | 20 | 0 | 80 | 250 | 0.1 | Dispersion Pad |
| 4 | 0 | 0 | 100 | 250 | 0.1 | Dispersion Pad |

ADCOTE 50T4990 is the same binder as PRIMACOR 4990
NB416 is a southern softwood.

Sample Preparation Procedure (Codes 1,2 & 3)

1. Spray PRIMACOR on air entrained fibers for 8 minutes
2. May add 1.74% surfactant based on PRIMACOR weight, but it is not necessary to do so
3. Mix SAP with wet coated fibers for 20 seconds
4. Deposit wet coated fibers+SAP in a loose pile and air dry at room temperature for 24 hours

Sample Testing Protocol

Test each of sample Codes 1 and 2 disposed over each of sample Codes 3 and 4. Insert pads (Codes 1 and 2) are in vertical alignment with the dispersion pads (Codes 3 and 4) such that the insult liquid passes through the insert pads first.

Binder fibers used to produce these samples were polypropylene type PF015 made by Montell USA. The wetting agent was MASIL SF-19 made by PPG Industries. The amount added was 2.0% by total weight PF015 and MASIL SF-19. Fluff pulp was CR-1654 made by US Alliance Coosa, and the superabsorbent was FAVOR 880 by Stockhausen.

Samples Based Upon Peniak, U.S. Pat. No. 4,560,372

Samples were prepared by taking a nonwoven material comprising polyester and bicomponent fiber with a void volume of 10 cc/g @0.01 psi and a basis weight of less than about 150 gsm and distributing 50% by weight superabsorbent, e.g. FAVOR 880, onto one surface based upon weight of the nonwoven material. A layer of tissue having a surface area equal to that of the nonwoven material was weighed out and placed over the surface of the nonwoven material containing the largest amount of superabsorbent. 10 to 50% moisture based on the combined weight of the nonwoven material, superabsorbent and tissue was added and the resulting layered structure compressed under a load of 200 to 500 psi. Machine direction rows of 0.5" slits spaced 0.25" apart were applied after which the sample was pulled in the cross direction to open up the slits to provide the apertures.

SUMMARY OF THE INVENTION

It is one object of this invention to provide an absorbent composite material suitable for use in personal care absorbent products, such as diapers, training pants, adult incontinence garments, and the like, having improved integrity, resistance to wet collapse, shape retention, and uptake rate.

It is another object of this invention to provide an absorbent composite material having the capability of serving as a controlled rate retention material.

It is yet another object of this invention to provide an absorbent composite material having the capability of slow-

Samples Based Upon GB 2 284 551

| Code | % SAP | % Binder | % Staple Fiber | GSM | Density $g/in^2$ | SAP type | Staple Fiber Type | Binder Type |
|---|---|---|---|---|---|---|---|---|
| 2 | 75 | 10 | 15 | 641 | 0.2 | Favor 880 | Fluff pulp | Polypropylene PP-PF015 |
| 3 | 29 | 41 | 30 | 280 | 0.2 | Favor 880 | Fluff Pulp | Polypropylene PP-PF015 | ing down the absorption rate of superabsorbents which normally have inherently high absorption rates.

It is another object of this invention to provide an absorbent composite material having an Absorption Time Index greater than the Absorption Time Index of known materials.

These and other objects of this invention are achieved by an absorbent composite material having an Absorption Time Index greater than about 10 minutes comprising a fibrous absorbent material selected from the group consisting of fluff pulp, synthetic fibers, natural fibers, and combinations thereof, a superabsorbent material having a superabsorbent Absorption Time Index of less than about 5 minutes, and a binding agent, the binding agent binding at least a portion of the fibers of the fibrous absorbent material. The fibrous absorbent material comprises in the range of about 10% to about 90% by weight of the absorbent composite material and the superabsorbent material comprises in the range of about 10% to about 90% by weight of the absorbent composite material. The binding agent is preferably a tacky adhesive or tacky polymeric fibers.

BRIEF DESCRIPTION OF THE DRAWINGS

These and other objects and features of this invention will be better understood from the following detailed description taken in conjunction with the drawings wherein.

DESCRIPTION OF PREFERRED EMBODIMENTS

Methods for determining the Absorption Time Index of a material vary depending upon the material being tested. The absorbent composite material of this invention was tested in accordance with the following procedure. A funnel fitted with a 15 micron average pore size fritted glass plate (e.g. PYREX® No. 36060 Buchner funnel with fritted disk) is connected to a 0.9% NaCl saline reservoir, which is sitting on a balance. The balance is connected to a data processing device so that the amount of liquid in the reservoir can be recorded as a function of time. A 504 gram brass disk having a diameter of 2.75 inches is used to apply a 0.2 psi pressure to the sample, a composite material disk also having a diameter of 2.75 inches. The height of the funnel is adjusted so that the upper surface of the fritted glass disk is the same height as the liquid surface in the reservoir. The data processing device is started so as to read the output of the balance. A sample to be tested, together with the plastic disk, is placed on the fritted glass disk. The absorption of liquid by the sample is then measured for 200 minutes. Analysis of the data involves plotting of the ratio of absorption in grams to the final absorption in grams as a function of time to obtain a curve from which the Absorption Time Index can be determined.

For determining the Absorption Time Index for superabsorbent, a somewhat different method is employed due to the different physical and chemical characteristics of the superabsorbent. In this case, the sample holder comprises a cylindrical tube of about 1.5 inches high having a 1-inch inside diameter. A 100 mesh stainless steel screen is attached to the bottom of the tube. A plastic container serves as a sample holder receiver and is connected to a 0.9% saline reservoir, which is sitting on a balance connected to a data processing device. A 3.3 gram plastic disk having a diameter of 0.95 inches is used to apply a pressure of 0.01 psi to the sample. In this case, the sample is 0.160 grams of superabsorbent material. The height of the sample holder receiver is adjusted so that its bottom is at the same height as the liquid surface in the reservoir. The data processing device which processes the output from the balance is started and the sample, together with the plastic disk, is placed on the sample holder receiver. In this case, absorption of fluid by the sample is measured for 60 minutes, after which the data is processed as before.

The material of this invention provides improved absorbent composites that are particularly suitable for use in personal care absorbent articles, such as baby diapers, training pants, adult incontinence products, and the like. The absorbent composite material of this invention utilizes a tacky adhesive and/or tacky polymeric fibers to bind fluff pulp and various synthetic and natural fibers, for example cellulose acetate, rayons, polypropylene, etc. to produce absorbent cores having improved integrity, resistance to wet collapse, shape retention and uptake rate for use in the aforementioned personal care absorbent products. In accordance with a particularly preferred embodiment of this invention, the absorbent composite material also comprises a superabsorbent material. Various synthetic and natural fibers used in the material of this invention may be selected to enhance liquid distribution.

The superabsorbent/fluff absorbent composites in conventional personal care absorbent articles such as diapers tend to collapse when wet, resulting in reduced absorbent uptake rate, integrity and poor shape retention. As a result, the potential for product leakage arising from multiple insults is increased. In addition, these absorbent core materials are inefficient due to the relatively low amount of liquid absorbed per gram of absorbent. Consequently, they have limited ability to distribute liquid away from the target zone.

Figure 1:
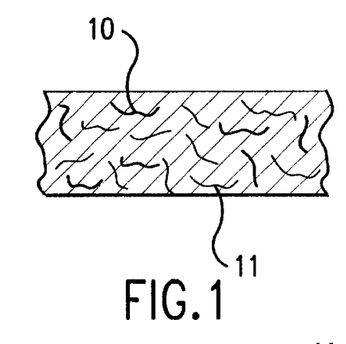
FIG. 1 is a cross sectional view of a homogeneous absorbent composite material in accordance with one embodiment of this invention.

The concentration of liquid around the insult target area causes the product to bulge and sag due to the weight of the liquid. In addition, once the limited capacity of the target area is reached, there is further increased potential for product leakage. Furthermore, the heavily saturated absorbent material in contact with the skin may cause skin irritation. Finally, wet and dry superabsorbent material particles often migrate from these conventional superabsorbent material/fluff absorbent cores and become attached to the skin of the wearer of the absorbent article. The material of this invention which addresses these problems is an absorbent composite material having an Absorption Time Index greater than about 10 minutes comprising a fibrous absorbent material selected from the group consisting of fluff pulp, synthetic fibers, natural fibers, and combinations thereof, a superabsorbent material having a superabsorbent Absorption Time Index of less than about 5 minutes, and a binding agent, wherein the binding agent binds at least a portion of the fibers of the fibrous absorbent material. In accordance with a preferred embodiment, the Absorption Time Index of the absorbent composite material of this invention is in the range of about 10 minutes to 120 minutes and most preferably is in the range of about 15 minutes to about 60 minutes. The basis weight of the absorbent composite material of this invention is in the range of about 100 $g/m^2$ to about 1000 $g/m^2$. In accordance with one preferred embodiment of this invention, the fibrous absorbent material is pulp fibers. The fibrous absorbent material comprises preferably in the range of about 10% to about 90% by weight of said absorbent composite material, more preferably about 20% to about 80% by weight of said absorbent composite material, and most preferably about 30% to about 60% by weight of said composite material. Said superabsorbent material preferably comprises about 10% to 90%, more preferably about 20% to about 80%, and most preferably about 40% to about 70% by weight of said absorbent composite material. The binding agent is preferably a tacky adhesive or tacky polymeric fibers which bond with the non-tacky fibrous absorbent materials used in personal care absorbent articles. In accordance with one preferred embodiment of this invention, the absorbent composite material comprises a substantially homogeneous absorbent web of about 0.05% to about 5% by weight of a tacky adhesive and/or tacky polymeric fibers blended with, and substantially bonded to, non-tacky fibrous absorbent materials such as fluff pulp, cellulose acetate, rayons, staple fibers, and the like. FIG. 1 shows a homogeneous absorbent composite material in accordance with one embodiment of this invention comprising tacky polymeric fibers 10 bonded to non-tacky fibers 11.

Figure 3:
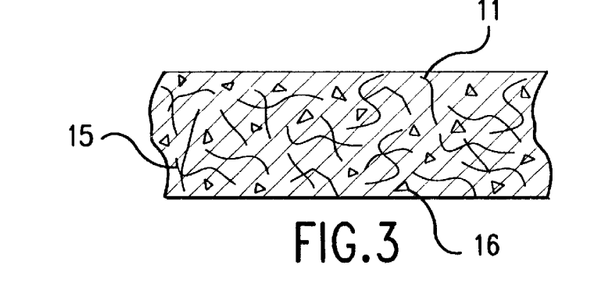
FIG. 3 is a cross sectional view of a homogeneous absorbent composite material comprising particulate superabsorbent materials.
Figure 4:
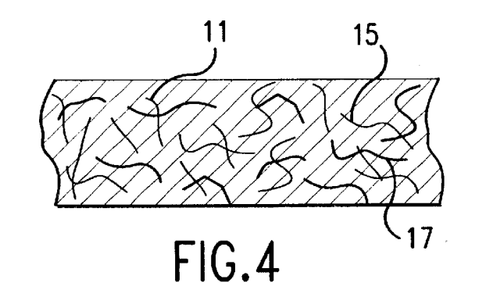
FIG. 4 is a cross sectional view of a homogeneous absorbent composite material comprising fibrous superabsorbent materials in accordance with one embodiment of this invention.
Figure 5:
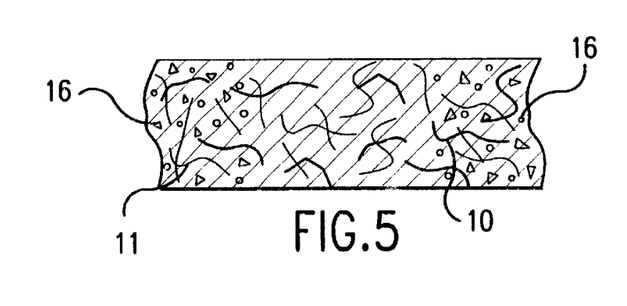
FIG. 5 is a cross sectional view of an absorbent composite material wherein the superabsorbent material is not uniformly distributed therethrough.

The superabsorbent materials may be in the form of particles 16 as shown in FIG. 3 or in the form of fibers 17 of various physical and functional absorption properties, as shown in FIG. 4. In addition, as shown in FIG. 5, the superabsorbent material, in accordance with one embodiment of this invention, is incorporated into the absorbent composite material in a non-uniform fashion resulting in some regions of the absorbent composite material having no superabsorbent material, some regions of the absorbent composite material having low concentrations of superabsorbent material, and some regions of the absorbent composite material having high concentrations of superabsorbent material.

Figure 2:
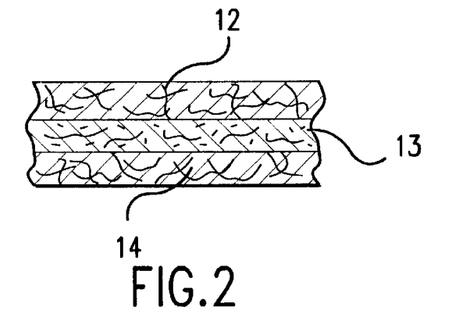
FIG. 2 is a cross sectional view of a layered absorbent composite material in accordance with one embodiment of this invention.

In accordance with one preferred embodiment of this invention, the absorbent composite material comprises a plurality of layers as shown in FIG. 2. In accordance with the embodiment shown in FIG. 2, the fibrous absorbent material forms a lower density layer 12, a higher density layer 14, and an intermediate bonding agent layer 13. In accordance with a particularly preferred embodiment of this invention, the lower density layer has a density of less than about 0.06 g/cc and a basis weight in the range of about 50 $g/m^2$ to about 200 $g/m^2$. The higher density layer has a density greater than about 0.08 g/cc, preferably in the range of about 0.08 g/cc to about 1.5 g/cc. The lower density layer 12 and the higher density layer 14, as shown in FIG. 2, are lined in the vertical direction and bonded together by a layer of tacky adhesive and/or polymeric fibers 13 disposed therebetween. In accordance with this embodiment, some of the tacky fibers are embedded into the lower and higher density layers to provide an integrated absorbent composite having reduced potential for interfacial separation between the layers, thereby providing enhanced absorbent performance.

The tacky adhesive and/or tacky polymeric fibers bind the absorbent composite material structure together to enhance absorbent integrity and shape retention. In addition, through a proper selection of tacky adhesive and polymeric fibers, along with the non-tacky component, for example curly cellulose, absorbent composites with enhanced uptake rate may be produced. We have found, for example, that an absorbent composite material in accordance with one embodiment of this invention comprising up to 5% by weight hot melt adhesive, 35% by weight superabsorbent, and 60–65% by weight absorbent fluff pulp had an improved integrity in the range of 109–678% compared to superabsorbent/fluff absorbent composite materials without tacky adhesives.

As previously stated, the absorbent composite material of this invention functions as a controlled rate retention material. The structure and materials comprising the absorbent composite material of this invention exhibit a controlled release swelling mechanism which is suitable for use in diapers and other personal care absorbent products. The absorbent composite material may be embossed to further favorably influence integrity and fluid uptake rate. In accordance with one particularly preferred embodiment, the absorbent composite material of this invention has an embossed area, defined as the total percentage of area that has been compressed by the embossing pattern, of less than about 50%.

To create personal care absorbent products such as diapers having desired liquid handling, retention materials exhibiting the desired fluid uptake rates are required. In certain designs, slow retention materials are a necessity. The absorbent composite material of this invention provides a new class of retention composites which can be engineered to achieve desired fluid uptake rates. The absorbent composite material of this invention uses conventional materials to achieve a thin and efficient structure having better fit, desired uptake rate, excellent integrity, and controlled fluid placement. Additionally unique features of the absorbent composite material of this invention include a comfortably soft feel during wear and a cut-and-place option for diaper processing. The absorbent composite material of this invention also has the advantage of controlling uptake rates without the need for low permeability wrap materials.

By controlling the various components comprising the absorbent composite material of this invention and their structure, the controlled release swelling mechanism of the material can also be influenced. Factors affecting this mechanism include:

1) Absorbent filling—superabsorbent, fluff, and adhesive types;
2) Bonding agent—adhesive bonding agents versus synthetic fibers;
3) Embossing type, pattern and coverage; and
4) Basis weight—ratio of superabsorbent/fluff/adhesive.

These elements can be varied to produce an absorbent composite material in accordance with this invention having a range of absorbency mechanisms from immediate to delayed fluid absorption. The absorbent composite material of this invention provides the greater fluid distribution and material utilization needed for personal care absorbent products. Furthermore, data show that the superabsorbent, fluff and adhesive drastically affect the materials fluid absorption rate.

EXAMPLE I

In this example, commercial superabsorbent, fluff, and adhesive were used to construct absorbent composite material structures in accordance with this invention. These raw materials included STOCKHAUSEN FAVOR 870M® from Stockhausen, Greensboro, N.C.; CR1654 Pulp from Kimberly-Clark Corporation, Neenah, Wis.; and NATIONAL STARCH HOT MELT ADHESIVE 5541® from National Starch, Bridgewater, N.J. NATIONAL STARCH HOT MELT ADHESIVE 5541 is based on a styrene-butadiene-styrene (SBS) block-copolymer. Other suitable adhesives also from National Starch include Grades 3456, 70-3998 and 33-2858. Both homogeneous and layered absorbent composite structures were made. These composites had superabsorbent levels in the range of about 30% to 60% by weight and fluff levels from about 40% to about 70% by weight. In addition, all of the composites had add-on levels of hot melt adhesive ranging from about 5% to about 20% by weight. Some of the composites were further embossed with patterns so as to impact rate behaviors.

Figure 6:
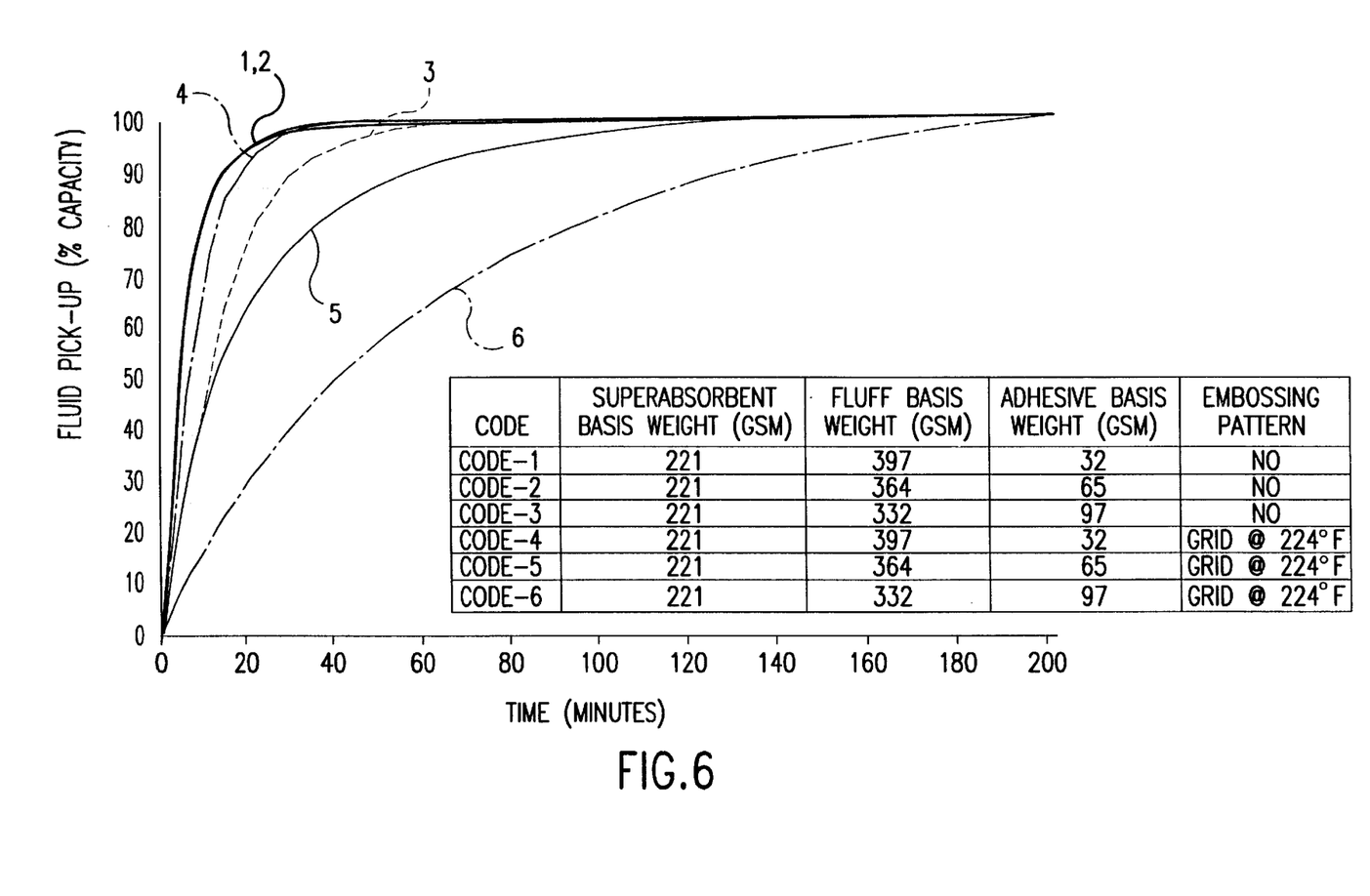
FIG. 6 is a diagram showing the effect of adhesive levels and embossing patterns on the fluid uptake of the absorbent composite material of this invention.

FIG. 6 shows the effect of adhesive levels and embossing patterns on the fluid pickup of the absorbent composite materials. Data lines designated as Codes 1, 2 and 3 correspond to absorbent composite materials which were not embossed whereas data lines designated by Codes 4, 5 and 6 correspond to absorbent composite materials which were thermally embossed with a grid-like pattern wherein line width was approximately $\frac{1}{32}$ inch, line spacing was about $\frac{1}{4}$ inch and embossed area was about 22%. The data show that higher adhesive levels and thermal embossing tend to reduce the absorbency rate of the composite material.

EXAMPLE II

To determine the effect of composition, homogeneity, and thermal/pressure treatment on the absorbency properties of the absorbent composite material of this invention, samples having superabsorbent/fluff ratios in the range of 30/70 to 60/40 with hot melt adhesive add-on levels ranging from 10 to 20% by weight were prepared. Samples having higher adhesive levels, higher fluff content, and lower superabsorbent levels were found to have slower uptake rates. Overall, the effect of adhesive on uptake rates was found to be more dramatic than that of superabsorbent or fluff. By comparison of uniform absorbent composite materials wherein adhesive is uniformly distributed therethrough and layered absorbent composite materials in which adhesive is disposed between the layers of fibrous absorbent material, we found that the homogeneous/uniform embodiment provided a slower uptake rate than the layered embodiment.

In order to determine the effect of thermal/pressure treatment on the absorbent composite material of this invention, four treatment methods were employed as follows:

1) No treatment;
2) Thermal/pressure embossed grid pattern;
3) Thermal/pressure embossed point pattern;
4) Thermal/pressure embossed flat pattern.

Figure 7:
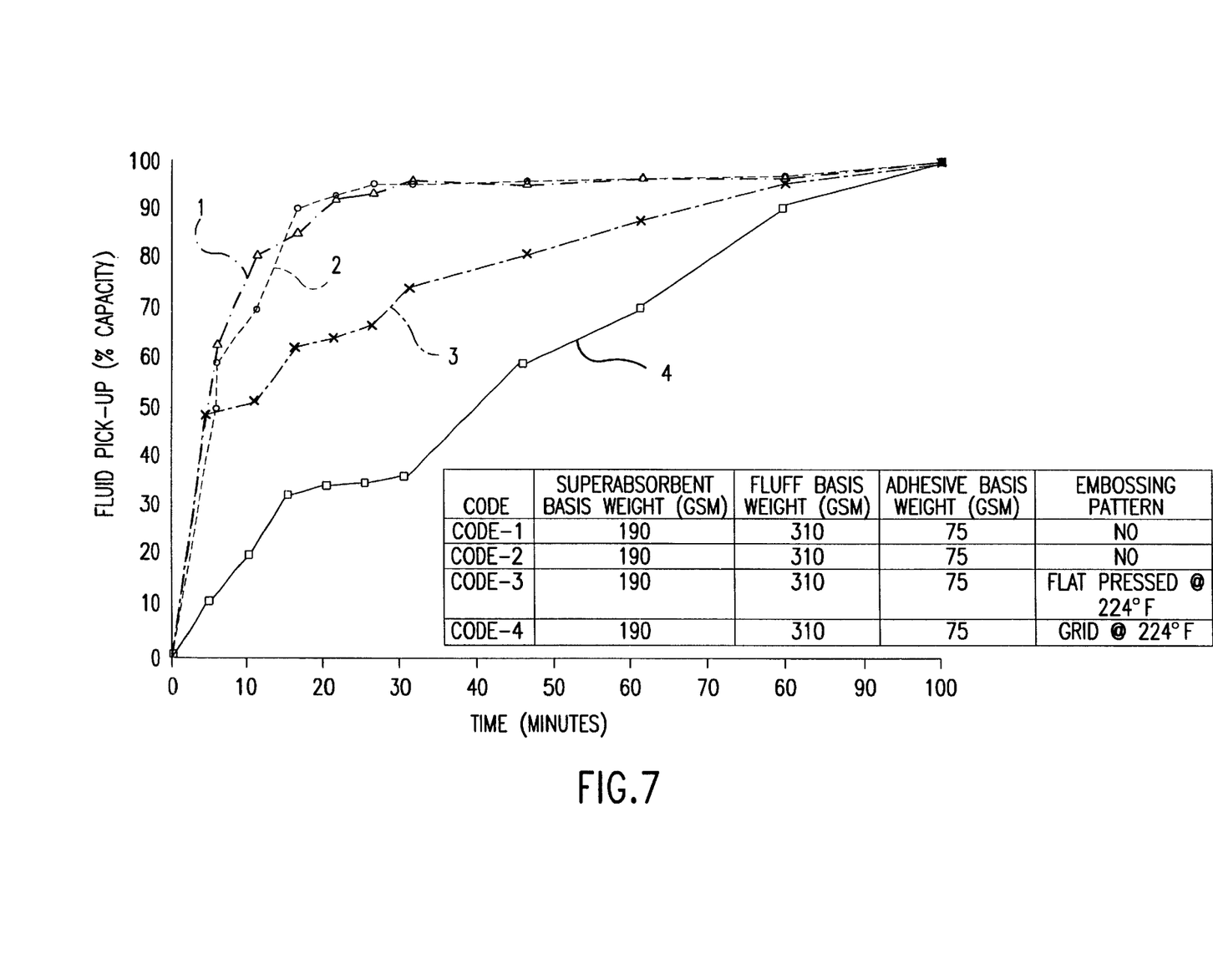
FIG. 7 is a diagram showing the effect of various thermal/pressure treatments on fluid uptake by the absorbent composite material of this invention.

The point and grid patterns created a quilt/pocketed surface. In the simulated forced flow condition of the test procedure, the composites were under a pressure of 0.3 psi while exposed to excess saline. After 90 minutes, all of the samples had reached similar capacity, albeit at different rates. These results are shown in FIG. 7. During the course of these tests, we noted that the point pattern (less pronounced quilted pockets) made up of $\frac{1}{32}"\times\frac{1}{32}"$ point sizes, with a $\frac{1}{4}$-inch distance between neighboring points and an embossed area of 1.2% was less effective than the grid pattern in reducing the fluid pick up rate, but more effective than the flat pressed pattern.

Figure 8:
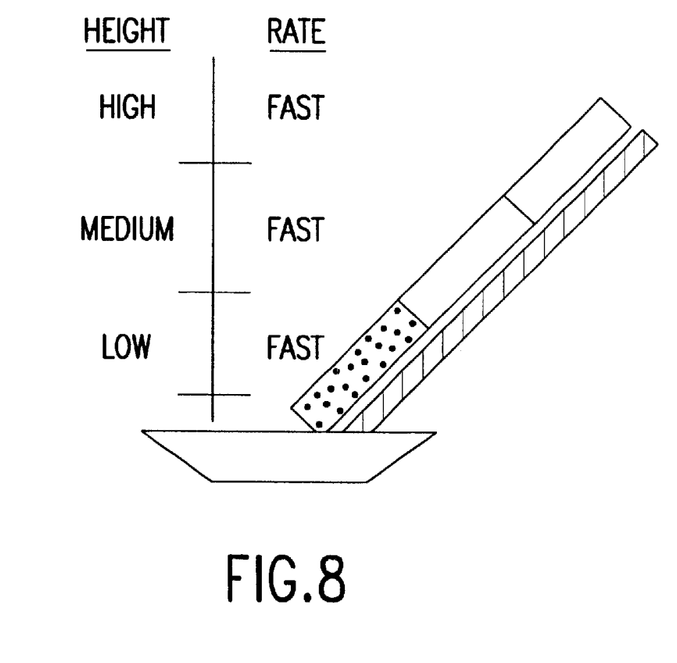
FIG. 8 is a diagram showing the effect of composite uptake rate on fluid distribution and material utilization for a typical homogeneous structure.
Figure 9:
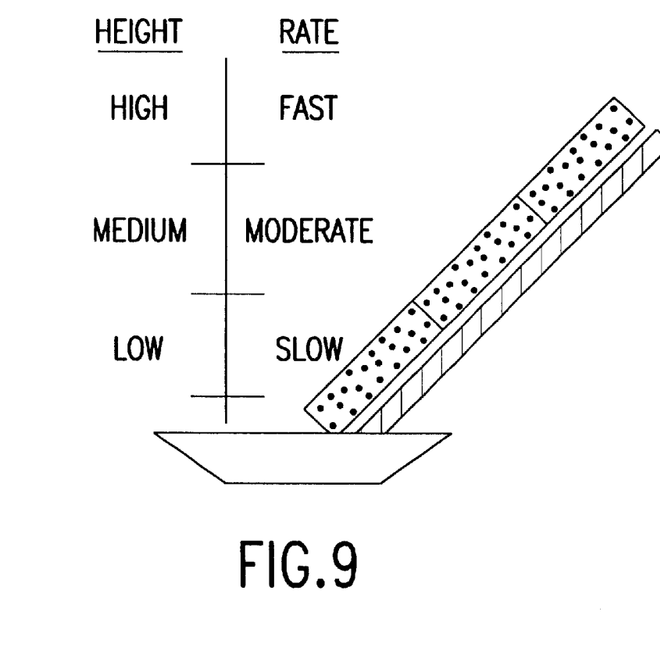
FIG. 9 shows the effect of composite uptake rate on fluid distribution and material utilization for an absorbent composite material in accordance with this invention.

A slow absorbent composite material has the potential for providing higher absorbency rates for later insults and compensate for product performance deterioration typically associated with later insults. FIGS. 8 and 9 show the effect of composite uptake rate on fluid distribution and material utilization. As shown, the absorbent composite materials were divided into 3 zones, low, medium, and high heights. The absorbency rates of each zone were varied to control fluid placement. FIG. 7 shows that a typical homogeneous structure containing superabsorbent and fluff, in which all of the zones have fast fluid uptake rates, achieves a non-uniform fill and does not utilize the entire product. By comparison, FIG. 8 shows an absorbent composite material structure having uniform fill and material utilization. We found that the absorbent composite materials of this invention were most efficient when composed of the following zones:

1) Slow uptake rate, low height zone;
2) Moderate uptake rate, medium height zone; and
3) Fast uptake rate, and high height zone.

Thus, it is apparent that when the variables are appropriately selected and balanced, the absorbent composite material of this invention provides the greater fluid distribution and material utilization necessary for personal care absorbent products through its controlled swelling mechanism.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. An absorbent composite material comprising:
   a fibrous absorbent material selected from the group consisting of fluff pulp, synthetic fibers, natural fibers, and combinations thereof;
   a superabsorbent material having a Superabsorbent Absorption Time Index of less than about 5 minutes; and
   a binding agent, said binding agent binding at least a portion of the fibers of said fibrous absorbent material;
   said absorbent composite material having an Absorption Time Index greater than about 10 minutes.

2. An absorbent composite material in accordance with claim 1, wherein said fibrous absorbent material comprises in a range of about 10% to about 90% of said absorbent composite material.

3. An absorbent composite material in accordance with claim 1, wherein said fibrous absorbent material comprises in a range of about 20% to about 80% of said absorbent composite material.

4. An absorbent composite material in accordance with claim 1, wherein said fibrous absorbent material comprises in a range of about 30% to about 60% of said absorbent composite material.

5. An absorbent composite material in accordance with claim 1, wherein said superabsorbent material comprises in a range of about 10% to about 90% by weight of said absorbent composite material.

6. An absorbent composite material in accordance with claim 1, wherein said superabsorbent material comprises in a range of about 20% to about 80% by weight of said absorbent composite material.

7. An absorbent composite material in accordance with claim 1, wherein said superabsorbent material comprises in a range of about 40% to about 70% by weight of said absorbent composite material.

8. An absorbent composite material in accordance with claim 1, wherein said fibrous absorbent material is pulp fibers.

9. An absorbent composite material in accordance with claim 1, wherein said binding agent comprises a tacky adhesive.

10. An absorbent composite material in accordance with claim 1, wherein said binding agent comprises a plurality of tacky polymeric fibers.

11. An absorbent composite material in accordance with claim 1, wherein a basis weight of said material is in a range of about 100 g/m$^2$ to about 1000 g/m$^2$.

12. An absorbent composite material in accordance with claim 1, wherein said Absorption Time Index is in a range of about 10 minutes to about 120 minutes.

13. An absorbent composite material in accordance with claim 1, wherein said Absorption Time Index is in a range of about 15 minutes to about 60 minutes.

14. An absorbent composite material in accordance with claim 1, wherein said fibrous absorbent material is formed as a lower density layer having a lower density layer basis weight in a first range of about 50 g/m$^2$ to about 200 g/m$^2$ and a higher density layer having a higher density layer basis weight in a second range of about 100 g/m$^2$ to about 500 g/m$^2$, said lower density layer and said higher density layer aligned in a vertical direction and bonded together by said binding agent.

15. An absorbent composite material in accordance with claim 1 comprising in a range of about 0.5% to about 50% by weight of an adhesive said binding agent.

16. An absorbent composite material in accordance with claim 1, wherein said at least one superabsorbent material is in particulate form.

17. An absorbent composite material in accordance with claim 1, wherein said at least one superabsorbent material is in a fibrous form.

18. An absorbent composite material in accordance with claim 1, wherein said at least one superabsorbent material is uniformly distributed throughout said absorbent composite material.

19. An absorbent composite material in accordance with claim 1, wherein said at least one superabsorbent material is distributed nonuniformly within said absorbent composite material.

20. An absorbent composite material in accordance with claim 19, wherein said at least one superabsorbent material is nonuniformly distributed in a lateral plane throughout said absorbent composite material.

21. An absorbent composite material in accordance with claim 19, wherein said at least one superabsorbent material is nonuniformly distributed in a z-direction throughout said absorbent composite material.

22. An absorbent composite material in accordance with claim 1 further comprising at least one embossed pattern covering an embossed area in a range of about 0.01% to about 50%.

23. An absorbent composite material in accordance with claim 1, wherein said binding agent is uniformly distributed throughout said fibrous absorbent material.

24. A personal care absorbent article comprising:
an absorbent composite material having an Absorption Time Index greater than about 10 minutes and comprising a fibrous absorbent material selected from the group consisting of fluff pulp, synthetic fibers, natural fibers, and combinations thereof, a superabsorbent material having a Superabsorbent Absorption Time Index of less than about 5 minutes, and a binding agent, said binding agent binding at least a portion of the fibers of said fibrous absorbent material.

25. A personal care absorbent article in accordance with claim 24, wherein said fibrous absorbent material comprises in a range of about 10% to about 90% of said absorbent composite material.

26. A personal care absorbent article in accordance with claim 24, wherein said superabsorbent material comprises in a range of about 10% to about 90% by weight of said absorbent composite material.

27. A personal care absorbent article in accordance with claim 24, wherein said fibrous absorbent material is pulp fibers.

28. A personal care absorbent article in accordance with claim 24, wherein said binding agent comprises a tacky adhesive.

29. A personal care absorbent article in accordance with claim 24, wherein said binding agent comprises a plurality of tacky polymeric fibers.

30. A personal care absorbent article in accordance with claim 24, wherein a basis weight of said material is in a range of about 100 g/m$^2$ to about 1000 g/m$^2$.

31. A personal care absorbent article in accordance with claim 24, wherein said Absorption Time Index is in a range of about 10 minutes to about 120 minutes.

32. A personal care absorbent article in accordance with claim 24, wherein said Absorption Time Index is in a range of about 15 minutes to about 60 minutes.

33. A personal care absorbent article in accordance with claim 24, wherein said fibrous absorbent material is formed as a lower density layer having a lower density layer basis weight in a first range of about 50 g/m$^2$ to about 200 g/m$^2$ and a higher density layer having a higher density layer basis weight in a second range of about 100 g/m$^2$ to about 500 g/m$^2$, said lower density layer and said higher density layer aligned in a vertical direction and bonded together by said binding agent.

34. A personal care absorbent article in accordance with claim 24 comprising in a range of about 0.5% to about 50% by weight of an adhesive said binding agent.

35. A personal care absorbent article in accordance with claim 24, wherein said at least one superabsorbent material is uniformly distributed throughout said absorbent composite material.

36. A personal care absorbent article in accordance with claim 24, wherein said at least one superabsorbent material is distributed nonuniformly within said absorbent composite material.

37. A personal care absorbent article in accordance with claim 24 further comprising at least one embossed pattern covering an embossed area in a range of about 0.01% to about 50%.

38. A diaper comprising:
an absorbent composite material having an Absorption Time Index greater than about 10 minutes and comprising a fibrous absorbent material selected from the group consisting of fluff pulp, synthetic fibers, natural fibers, and combinations thereof, a superabsorbent material having a Superabsorbent Absorption Time Index of less than about 5 minutes, and a binding agent, said binding agent binding at least a portion of the fibers of said fibrous absorbent material.

39. A diaper in accordance with claim 38, wherein said binding agent comprises at least one of a tacky adhesive and tacky polymeric fibers.

40. A diaper in accordance with claim 38, wherein said fibrous absorbent material comprises in a range of about 10% to about 90% of said absorbent composite material.

41. A diaper in accordance with claim 38, wherein said superabsorbent material comprises in a range of about 10% to about 90% by weight of said absorbent composite material.

42. A diaper in accordance with claim 38, wherein a basis weight of said material is in a range of about 100 $g/m^2$ to about 1000 $g/m^2$.

43. A diaper in accordance with claim 38, wherein said fibrous absorbent material is pulp fibers.

44. A diaper in accordance with claim 38 further comprising in a range of about 0.5% to about 50% by weight of an adhesive said binding agent.

45. A diaper in accordance with claim 38, wherein said fibrous absorbent material is formed as a lower density layer having a lower density layer basis weight in a first range of about 50 $g/m^2$ to about 200 $g/m^2$ and a higher density layer having a higher density layer basis weight in a second range of about 100 $g/m^2$ to about 500 $g/m^2$, said lower density layer and said higher density layer aligned in a vertical direction and bonded together by said binding agent.

46. A diaper in accordance with claim 38, wherein said absorbent composite material comprises in a range of about 0.5% to about 50% by weight of an adhesive said binding agent, about 30 to about 70% by weight of said at least one superabsorbent material, and about 30 to about 60% by weight of said fluff pulp.

47. An absorbent composite material comprising:
   a fibrous absorbent material selected from the group consisting of fluff, pulp, synthetic fibers, natural fibers, and combinations thereof;
   a superabsorbent material having a Superabsorbent Absorption Time Index of less than about 5 minutes;
   a binding agent, said binding agent binding at least a portion of the fibers of said fibrous absorbent material; and
   at least one embossed pattern covering an embossed area in a range of about 0.1% to about 50%;
   said absorbent composite material having an Absorption Time Index greater than about 10 minutes.

\* \* \* \* \*